United States Patent
Yin et al.

(10) Patent No.: US 10,976,396 B2
(45) Date of Patent: Apr. 13, 2021

(54) METHODS FOR QUANTIFYING TRABECULAR RESERVE USING MAGNETIC RESONANCE ELASTOGRAPHY

(71) Applicant: Mayo Foundation for Medical Education and Research, Rochester, MN (US)

(72) Inventors: Ziying Yin, Rochester, MN (US); Richard Ehman, Rochester, MN (US); Yi Sui, Rochester, MN (US); John Huston, III, Rochester, MN (US); Meng Yin, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 453 days.

(21) Appl. No.: 16/002,417

(22) Filed: Jun. 7, 2018

(65) Prior Publication Data

US 2019/0011522 A1    Jan. 10, 2019

Related U.S. Application Data

(60) Provisional application No. 62/516,409, filed on Jun. 7, 2017.

(51) Int. Cl.
*G01R 33/563* (2006.01)
*A61B 5/00* (2006.01)
(Continued)

(52) U.S. Cl.
CPC ...... *G01R 33/56358* (2013.01); *A61B 5/0051* (2013.01); *A61B 5/055* (2013.01);
(Continued)

(58) Field of Classification Search
CPC .......... G01R 33/56358; G01R 33/4828; A61B 5/7285; A61B 5/7235; A61B 5/0051;
(Continued)

(56) References Cited

U.S. PATENT DOCUMENTS 5,592,085 A    1/1997 Ehman
5,825,186 A    10/1998 Ehman
(Continued)

OTHER PUBLICATIONS

Anderson AT, et al. Observation of direction-dependent mechanical properties in the humanbrain with multi-excitation MR elastography. J Mech Behav Biomed Mater. 2016;59:538-546.
(Continued)

*Primary Examiner* — Peter Luong
(74) *Attorney, Agent, or Firm* — Quarles & Brady LLP (57) ABSTRACT

Described here are systems and methods for evaluating the extent of brain-skull tethering, which may also be referred to as loss of trabecular reserve, in subjects using magnetic resonance elastography ("MRE"). The present disclosure describes a method for assessing progressive damage to arachnoid space ("SAS") trabeculae. The method generally includes measuring the relative movement between the brain and the skull using MRE. As one example, an MRE-based method named slip interface imaging ("SII") can be implemented. By measuring trabecular reserve in subjects who have a history of prior head trauma, the susceptibility of a given subject to future injury can be assessed.

35 Claims, 5 Drawing Sheets

(51) Int. Cl.
*A61B 5/055* (2006.01)
*G01R 33/48* (2006.01)
*A61B 5/113* (2006.01)
*A61B 5/08* (2006.01)
*A61B 5/0402* (2006.01)

(52) U.S. Cl.
CPC .......... *A61B 5/7235* (2013.01); *A61B 5/7285* (2013.01); *A61B 5/0402* (2013.01); *A61B 5/08* (2013.01); *A61B 5/0816* (2013.01); *A61B 5/113* (2013.01); *A61B 5/1135* (2013.01); *A61B 5/7292* (2013.01); *G01R 33/4828* (2013.01)

(58) Field of Classification Search
CPC ..... A61B 5/055; A61B 5/7292; A61B 5/1135; A61B 5/0816; A61B 5/08; A61B 5/0402; A61B 5/113
See application file for complete search history.

(56) References Cited

U.S. PATENT DOCUMENTS

| | | | |
|---|---|---|---|
| 6,037,774 A | 3/2000 | Felmlee | |
| 8,290,565 B2 | 10/2012 | Ehman | |
| 2013/0131490 A1* | 5/2013 | Huston, III | G01R 33/56358 600/410 |

OTHER PUBLICATIONS

Badachhape AA, et al. The relationship of three-dimensional human skull motion to brain tissue deformation in magnetic resonance elastography studies. J Biomech Eng. 2017;139.

Badachhape AA, et al. Relationships between scalp, brain, and skull motion estimated using magnetic resonance elastography. J Biomech. 2018;73:40-49.

ElSheikh M, et al. MR elastography demonstrates unique regional brain stiffness patterns in dementias. AJR Am J Roentgenol. 2017;209:403-408.

Mariappan, YK., et al., Cyclic motion encoding for enhanced MR visualization fo slip interfaces, J Magn Reson Imaging, 2009;30(4):855-863.

McGrath DM, et al. Evaluation of wave delivery methodology for brain MRE: insights from computational simulations. Magn Reson Med. 2017;78:341-356.

Murphy MC, et al. Preoperative assessment of meningioma stiffness using magnetic resonance elastography. J Neurosurg. 2013;118:643-648.

Murphy MC, et al. Decreased brain stiffness in Alzheimer's disease determined by magnetic resonance elastography. J Magn Reson Imaging. 2011;34:494-498.

Murphy MC, et al. Measuring the characteristic topography of brain stiffness with magnetic resonance elastography. PLoS One. 2013;8:e81668.

Murphy MC, et al. MR elastography of thebrain and its application in neurological diseases. Neuroimage. 2017. https://doi.org/10.1016/j.neuroimage.2017.10.008.

Reiss-Zimmermann M, et al. High resolution imaging of viscoelastic properties of intracranial tumours by multi-frequency magnetic resonance elastography. Clin Radiol. 2015;25:371-378.

Yin Z, et al. Slip interface imaging based on MR-elastography preoperatively predicts meningioma-brain adhesion. J Magn Reson Imaging. 2017;46:1007-1016.

Yin, Z, et al. "In vivo characterization of 3D skull and brain motion during dynamic head vibration using magnetic resonance elastography." Magnetic resonance in medicine 80.6 (2018): 2573-2585.

Yin, Z., et al., Slip Interface Imaging Predicts Tumor-Brain Adhesion in Vestibular Schwannomas. Radiology. Nov. 2015;277(2):507-17.

* cited by examiner

METHODS FOR QUANTIFYING TRABECULAR RESERVE USING MAGNETIC RESONANCE ELASTOGRAPHY

CROSS-REFERENCE TO RELATED APPLICATIONS

This application claims the benefit of U.S. Provisional Patent Application Ser. No. 62/516,409, filed on Jun. 7, 2017, and entitled "METHODS FOR QUANTIFYING TRABECULAR RESERVE USING MAGNETIC RESONANCE ELASTOGRAPHY," which is herein incorporated by reference in its entirety.

STATEMENT REGARDING FEDERALLY SPONSORED RESEARCH

This invention was made with government support under EB001981 awarded by the National Institutes of Health. The government has certain rights in the invention.

BACKGROUND

Certain populations, such as military service members and athletes who play contact sports, are highly susceptible to repeated, but minor, head trauma. If these individuals could be examined routinely with this technique, medical staff could receive early warnings of future significant head injuries, which can facilitate their decisions on whether it is safe to "return-to-service" or "return-to-play."

Anatomically, from exterior to interior, the human head is mainly composed of scalp, skull, dura mater, arachnoid mater, pia mater, and brain. The space between the arachnoid mater and pia mater is called the subarachnoid space ("SAS"), which is filled with cerebrospinal fluid ("CSF") and the trabeculae. The SAS that includes CSF and trabeculae are of great importance in stabilizing the position of the brain during hear movement. This is due to an abundance of trabeculae and their stretching (e.g., web-like) shape from the arachnoid mater to the pia mater. When a head is subjected to an impact, the web-like SAS trabeculae serves as a damping element to protect the brain by providing tethering effects, thereby the impact could rapidly diminish. However, trabeculae could be over-stretched and gradually teared due to the repeated and minor head traumas. At this stage of medical examination, the typical medical imaging (MRI and CT) and neuropsychological assessment can be normal, but the damage to the trabeculae could be real. With the loss of this tethering effect, the brain is more likely to undergo the constant reciprocating coup-countercoup movement, consequently resulting in more severe and localized tissue damage. Therefore, the loss of trabecular reserve would make an individual more susceptible to future brain injury than one with fully reserved trabeculae.

SUMMARY OF THE DISCLOSURE

The present disclosure addresses the aforementioned drawbacks by providing a method for quantifying trabecular reserve with magnetic resonance imaging (MRI). A vibratory motion is applied to a subject's head to impart shear motions between a skull and a brain of the subject. Data are acquired with an MRI system using a pulse sequence that includes motion encoding gradients having a frequency synchronized with a frequency of the applied vibratory motion. Images are reconstructed from the acquired data, and mechanical properties of a sub-arachnoid space are computed from the reconstructed images. A report that indicates trabecular reserve in the subject is generated based on the mechanical properties of the sub-arachnoid space.

It is another aspect of the present disclosure to describe a method for quantifying nonlinear mechanical properties of a tissue using magnetic resonance imaging (MRI). A dual-frequency vibratory motion is applied to a subject to impart shear motions in a tissue of interest in the subject. The dual-frequency vibratory motion includes a first vibratory motion oscillating at a first frequency and a second vibratory motion oscillating at a second frequency that is greater than the first frequency. Data are acquired with an MRI system using a pulse sequence that includes motion encoding gradients having a frequency synchronized with the second frequency of the applied vibratory motion. Images are reconstructed from the acquired data, and mechanical properties of the tissue of interest are computed from the reconstructed images. A report that indicates the computed mechanical properties of the tissue of interest is generated.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

A system and method is disclosed for evaluating the extent of brain-skull tethering, which may also be referred to as loss of trabecular reserve, in subjects using magnetic resonance elastography ("MRE"). The present disclosure describes a method for assessing progressive damage to arachnoid space ("SAS") trabeculae. The method generally includes measuring the relative movement between the brain and the skull using MRE. By measuring trabecular reserve in subjects who have a history of prior head trauma, the susceptibility of a given subject to future injury can be assessed.

In some embodiments of the methods described in the present disclosure, a dual-frequency motion encoding scheme is provided for implementing MRE. In these instances, the MRE driver system is operated such that a small amplitude wave is coupled with a small-but-finite pre-deformation. As one example, the dual-frequency excitation can include a low-frequency excitation at a slower time scale to generate varying states of small-but-finite deformations on the imaging plane, and a second, higher-frequency vibratory excitation that is applied to superpose small-amplitude vibrations on the small-but-finite deformations caused by the low-frequency excitation. Use of a dual-frequency mode can provide additional advantages for assessing the mechanical properties of the brain and the brain-skull interaction.

In still other embodiments of the methods described in the present disclosure, a dual-saturation acquisition scheme is provided for implementing MRE. In such an acquisition, two separate scans can be performed, or a single scan can be performed in which the MRE data from the water signal and the fat signal are acquired sequentially by shifting the imaging central frequency automatically. The first acquires data with fat-suppression and the second acquires data with water-suppression. The first scan is used in the conventional manner to characterize mechanically induced motion in brain tissue. The second scan is used to separately estimate the skull motion. Following reconstruction, these two distinct data sets can be analyzed together to reveal the interactions between the skull and brain motion.

In still other embodiments of the methods described in the present disclosure, a dual-sensitivity motion encoding scheme is provided for implementing MRE. The dual-sensitivity motion encoding scheme simultaneously acquires phase images using both low-motion encoding and high-motion encoding during a single MRE exam. The low-sensitivity phase image is both temporally and spatially wrap-free and therefore can be used to guide unwrapping of the high-sensitivity phase image to estimate the full skull and brain motion.

In MRE, an external vibration source generates mechanical waves in a tissue that are used to characterize that tissue. For example, an active or passive acoustic driver is used to generate vibratory motion in the tissue of a subject under examination. The physical properties of tissue are measured using MRE by applying a stress via this vibratory motion and observing the resulting strain. By measuring the resulting strain, elastic properties of the tissue such as Young's modulus, Poisson's ratio, shear modulus, and bulk modulus can be calculated. Moreover, by measuring the strain in multiple directions, the elastic properties of the tissue can be completely defined.

The attenuation of the strain wave can also be estimated by observing the rate at which the strain decreases as a function of distance from the stress producing source. From this, the viscous properties of the gyromagnetic medium may be estimated. The dispersion characteristics of the medium can be estimated by observing the speed and attenuation of the strain waves as a function of their frequency.

Typically, a single slice is imaged with motion-encoding performed in three orthogonal directions in three different acquisitions. Imaging in other planes may also be performed, and multi-slice imaging is also possible. The data acquisition may be performed over several breath holds; however, the acquisition may also be respiratory gated so that the subject can breathe freely during the scan.

In some embodiments, of the methods described in the present disclosure, mechanical properties associated with the relative movement between a subject's brain and skull can be measured using MRE. As one example, vibratory motion can be induced in the subject's head, such that relative movements between the brain and skull are established. Mechanical properties are then measured based on phase contrast images obtained while the vibratory stimulus is applied. By monitoring the mechanical properties relative to reference measurements, which may be previous measurements from the same subject or measurements stored in a database, the subject's trabecular reserve can be assessed. In some embodiments of the methods described in the present disclosure, an MRE-based method named slip interface imaging ("SII") can be implemented for measuring the mechanical properties related to the relative movement between the brain and the skull. Techniques for SII are described in U.S. Pat. No. 8,290,565, which is herein incorporated by reference in its entirety.

As stated above, MRE is a noninvasive imaging technique that can be used to quantify the mechanical properties of soft tissues by a vibratory stimulus to a target tissue, obtaining phase contrast images while the vibratory stimulus is applied, and processing the images to compute mechanical properties of the tissue. Typically, small amplitude vibrations (e.g., amplitudes on the order of microns) are applied to the tissue. Under such small deformation and strains, conventional MRE focuses on the estimation of the second order elastic modulus (e.g., linear shear modulus) that represents the Hookean (i.e., linear) stress-strain behavior. However, biological tissues and their pathologies generally have a far more complex behavior than the simple linear law describes. In order to better understand pathologies, it would be advantageous to measure higher order parameters of nonlinearity (e.g., third-order and forth-order constants of nonlinearity elasticity).

For a small-amplitude shear wave that travels in a small-but-finite pre-deformed solid, the theory of linear viscoelasticity will generally apply. Based on this assumption, the linear shear modulus can be calculated at certain states of small-but-finite pre-deformations. When the wave propagation is coupled to different states of pre-deformation there will be a shift experienced by the linear shear modulus (i.e., shear wave speed). Thus, the shear nonlinearity of tissues can be revealed by analyzing the evolution of the linear shear modulus as a function of different small-but-finite pre-deformations by implementing a dual-frequency excitation.

Thus, in some other embodiments of the methods described in the present disclosure, a dual-frequency excitation can be used. Such implementations have application not only to assessing trabecular reserve, but in imaging other tissues and organ systems. As one example, dual-frequency MRE can also be used for measuring the mechanical properties in the liver.

Figure 1:
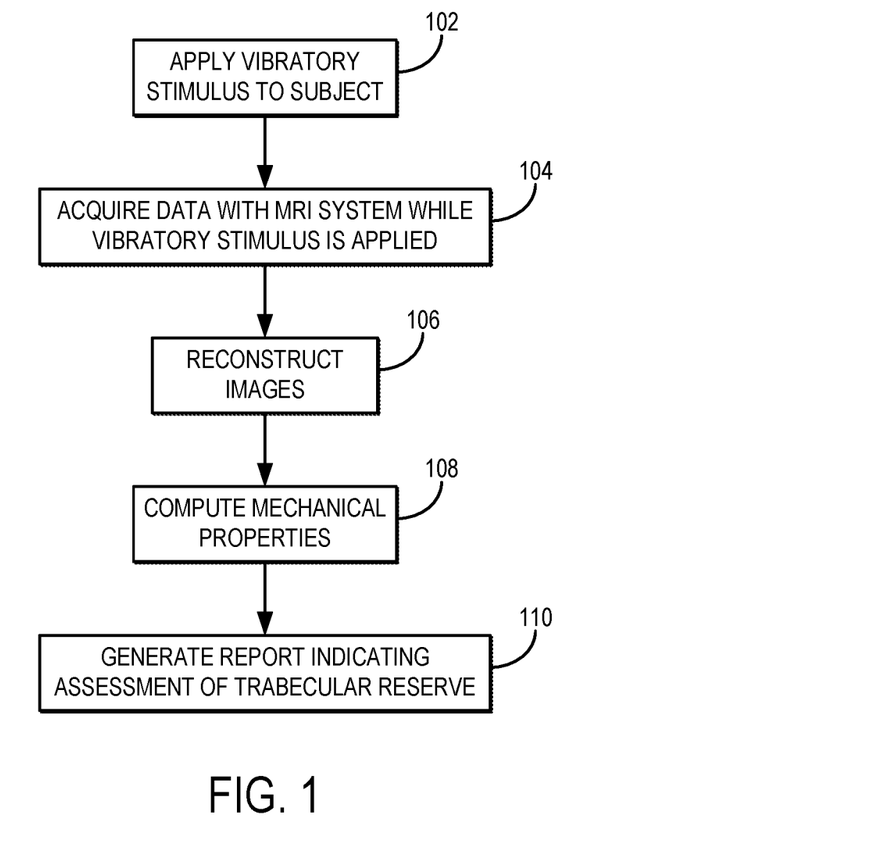
FIG. 1 is a flowchart setting forth the steps of an example method for quantifying trabecular reserve in a subject using magnetic resonance elastography.

Referring now to FIG. 1, a flowchart is illustrated as setting forth the steps of an example method for measuring trabecular reserve in a subject using magnetic resonance elastography ("MRE"). The method includes applying a vibratory stimulus to the subject's head, as indicated at step 102. For instance, an MRE driver system can be coupled to the subject's head and used to impart vibration energy to the subject's skull and brain, which in turn introduces relative shear motions (e.g., in the range of microns) between the brain and the skull.

As one example, the MRE driver system can include a pillow-like device that is positioned in a head coil. As another example, the MRE driver system can include a bite block that is vibrated, as described in U.S. Pat. No. 6,037,774, which is herein incorporated by reference in its entirety.

In some embodiments, the MRE driver system may be operated in a single-frequency mode, in which the vibratory stimulus is applied at a single excitation frequency. As one example, the excitation frequency may be 60 Hz. In some other embodiments, the MRE driver system may be operated in a dual-frequency mode, in which a small amplitude wave is coupled with a small-but-finite pre-deformation. As one example, the dual-frequency excitation can include a low-frequency excitation at a slower time scale (e.g., a frequency less than 5 Hz) to generate varying states of small-but-finite deformations on the imaging plane, and a second, higher-frequency vibratory excitation (e.g., a frequency of about 60 Hz) that is applied to superpose small-amplitude vibrations on the small-but-finite deformations caused by the low-frequency excitation. These methods are described in more detail below.

The use of a dual-frequency mode can provide additional advantages for assessing the brain's susceptibility to future injuries. The brain is largely suspended in cerebrospinal fluid ("CSF") and is mechanically connected to the skull through the web-like arachnoid trabeculae and subarachnoid vasculature. This mechanical connection system between the skull and the brain is referred as the pia-arachnoid complex ("PAC"), which protects the brain from an impact by acting as a mechanical tether between the brain and the skull that absorbs energy upon impact.

As the skull moves, the PAC tethers allow the brain to lag behind, and when the PAC tethers are sufficiently stretched to overcome the brain's inertia, the brain moves to catch up to the skull. However, the PAC connection can become over-stretched and gradually torn by repeated and minor or mild head injuries, even before symptoms develop. At this stage, the localized weak points on the PAC connection can be particularly susceptible to an increased risk of future injury.

It is contemplated that weakened PAC connections between the skull and the brain will result in different shear properties for different pre-deformation conditions, which can be analyzed using a dual-frequency excitation. By applying the low frequency shear excitation at the skull, the PAC could stretch or relax depending on the states of pre-deformation. By following the quantitative change of shear properties of brain tissue immediately interior to the skull, the transmission of the shear energy through the PAC can be assessed, which is distinguishable between a healthy brain and a brain that is more susceptible to future injury because of insufficient PAC connection.

Referring still to FIG. 1, data are acquired from the subject with a magnetic resonance imaging ("MRI") system while the vibratory stimulus is applied, as indicated at step 104. In general, the data are acquired using a pulse sequence that includes one or more motion encoding gradients that are synchronized with the applied vibratory stimulus such that the shear motions caused by the vibratory stimulus are encoded into the acquired magnetic resonance signals. As mentioned above, in some implementations data are acquired according to slip-interface imaging ("SII") techniques, such as those described in U.S. Pat. No. 8,290,565, which is herein incorporated by reference in its entirety.

For example, the frequency of the one or more motion encoding gradients can be synchronized with the frequency of the applied vibratory stimulus. In the case of a dual-frequency excitation, the one or more motion encoding gradients are synchronized with the second, higher-frequency excitation and not the lower-frequency vibration used to initiate the pre-deformation state.

In some implementations, acquired data include positive phase data and negative phase data. Positive phase data are acquired using an acquisition in which the polarity of the motion-encoding gradients is selected to be in-phase with the imparted motion. Similarly, negative phase data are acquired are acquired using an acquisition in which the polarity of the motion-encoding gradients is inverted, such that the motion-encoding gradients are out-of-phase with the imparted motion.

In other implementations, visualization of a propagating shear wave field is achieved by acquiring data at multiple time points. These time points can be chosen so as to be offset by a fraction of the period of the shear wave, in which the fraction is calculated to be:

$$\left(\frac{1}{n}\right) \cdot T; \quad (1)$$

where T is the period of the shear wave, and n is the number of images. In this manner, the acquired data represents a sequence of phase contrast images that are spaced substantially equally throughout the wave cycle, and therefore represent a temporal sample of the propagating wave caused by the applied vibratory stimulus.

In still other implementations, the data can be acquired using a dual-saturation acquisition, in which a first motion encoded data are acquired using fat-saturation and a second motion encoded data are acquired using water-saturation. As an example, the first motion encoded data can be acquired using a water-selective spatial-spectral ("SPSP") excitation and the second motion encoded data can be acquired using a fat-selective SPSP excitation. The first motion encoded data can represent brain signal (e.g., water-dominant signal) and the second motion encoded data can represent skull signal (e.g., fat-dominant signal). As described below in more detail, the water-dominant signals and the fat-dominant signals can be used to separately assess brain and skull displacements, respectively.

In still other implementations, the data can be acquired using a dual-sensitivity motion encoding scheme, which is described in more detail below.

Images are reconstructed from the acquired data, as indicated at step 106. For instance, wave images are reconstructed from the acquired data, which may include positive phase data and negative phase data sets. The intensity of each pixel in these wave images is determined by the phase imparted to nuclear spins moving in synchronism with the applied vibratory motion. This synchronous movement is a measure of the strain in the tissue under examination and the wave images, therefore, indicate the strain at corresponding locations in the tissue by the brightness of the pixels in the wave images. Reconstruction of the images may be performed as described in U.S. Pat. No. 5,592,085, and in U.S. Pat. No. 5,825,186, both of which are incorporated herein by reference in their entirety.

When the data acquired in step 102 are acquired according to SII techniques, the images can be processed to generate slip-interface images that indicate intravoxel phase dispersions at the interface between the brain and skull. Methods for reconstructing images according to SII techniques are described in U.S. Pat. No. 8,290,565, which is herein incorporated by reference in its entirety.

Mechanical properties can be computed from the reconstructed images, as indicated at step 108. As one example, an inversion algorithm is applied to the images to estimate mechanical properties, such as shear stiffness. For instance, mechanical properties of the tissue under examination can be computed in accordance with traditional MRE techniques, such as those described in U.S. Pat. No. 5,592,085, and in U.S. Pat. No. 5,825,186, both of which are incorporated herein by reference in their entirety. When images are acquired according to SII techniques, mechanical properties such as octahedral shear strain can be computed.

The computed mechanical properties can then be analyzed to measure or otherwise assess trabecular reserve in the subject, and a report indicating the assessment or measurement of trabecular reserve can be generated, as indicated at step 110. As an example, the mechanical properties can be compared to stored values associated with different states of trabecular reserve. For instance, in general, the loss of trabecular reserve will change the relative displacements between the brain and skull, and these changes can be assessed by comparing the measured mechanical properties to stored values associated with known levels of trabecular reserve.

In some instances, the mechanical properties can be compared with values previously computed for the same subject, in which case changes in the subject's own mechanical properties would indicate loss of trabecular reserve.

As mentioned above, in some instances data are acquired according to SII techniques and mechanical properties such as octahedral shear strain can be computed. By monitoring changes in octahedral shear strain from the relative freely movement between the skull and the brain, early warning of future head injury could be indicated by an abnormal brain-skull connection of the subject.

Having described an example method for assessing trabecular reserve using MRE, methods for dual-frequency MRE, which can be implemented to assess trabecular reserve as described above, are now described in more detail.

Figure 2:
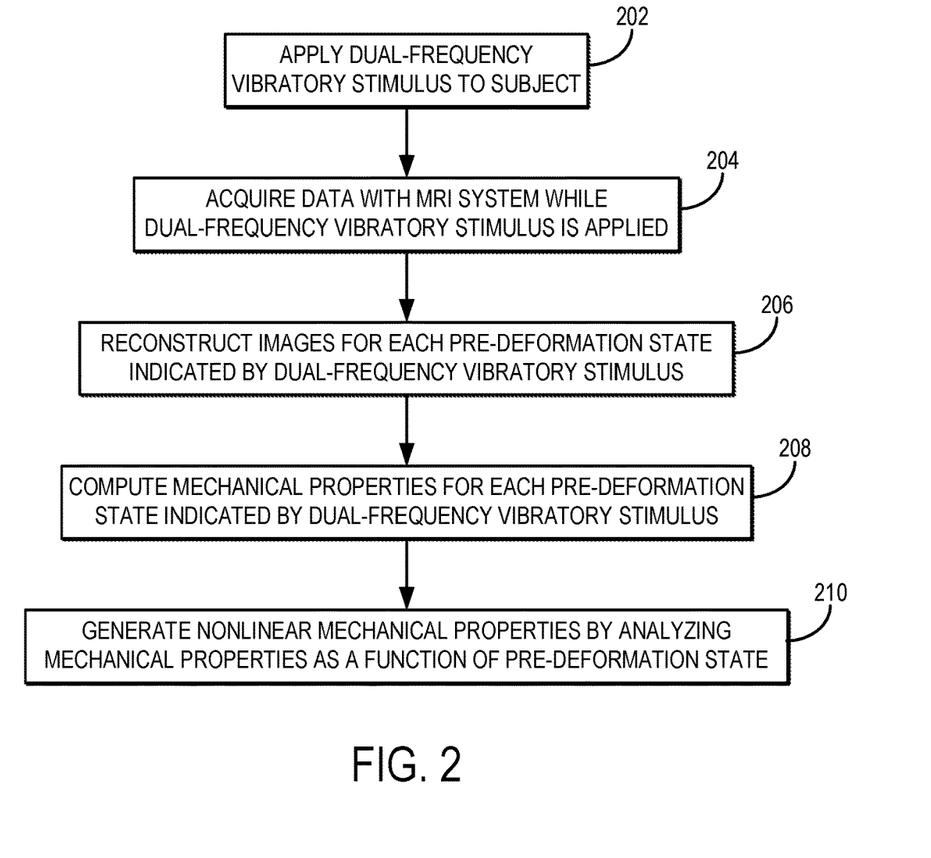
FIG. 2 is a flowchart setting forth the steps of an example method for quantifying nonlinear mechanical properties of a tissue by applying a dual-frequency vibratory motion to the tissue and imaging the vibratory motion with magnetic resonance elastography techniques.

Referring now to FIG. 2, a flowchart is illustrated as setting forth the steps of an example method for measuring mechanical properties in a tissue using dual-frequency MRE to facilitate the measurement of tissue nonlinearity. The method includes applying a dual-frequency vibratory stimulus to a subject, as indicated at step 202. In general, the dual-frequency vibratory stimulus can be applied with any suitable MRE driver system.

Figure 3:
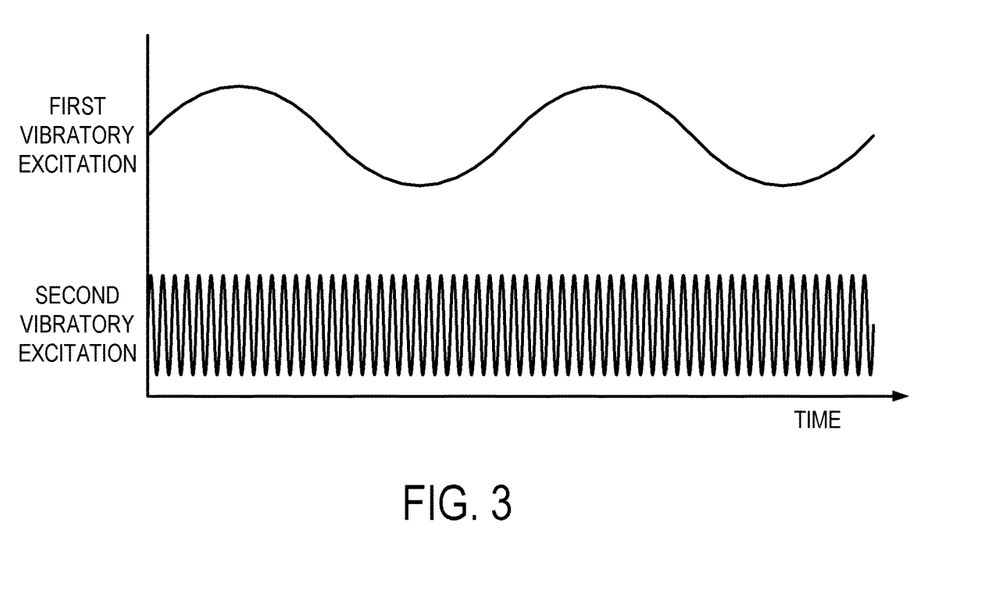
FIG. 3 shows an example of a low-frequency component and a high-frequency component of a dual-frequency vibratory excitation.

The dual-frequency vibratory stimulus includes a first vibratory excitation and a second vibratory excitation that is applied contemporaneously with the first vibratory excitation, as shown in FIG. 3. The first vibratory excitation is generally a low-frequency excitation, such as less than 5 Hz. The second vibratory excitation is applied at a higher frequency than the first vibratory excitation. As one example, the second vibratory excitation can be applied at 60 Hz. In the example shown in FIG. 3, the frequency of the first vibratory excitation is 2 Hz and the frequency of the second vibratory excitation is 60 Hz.

The first vibratory excitation is used to generate varying states of small-but-finite deformations in the tissue under examination. These small-but-finite deformations can represent certain physiological or pathological preloaded situations that the tissue under examination could experience. The second, higher-frequency vibratory excitation is applied to superpose small-amplitude vibrations on the small-but-finite deformations caused by the first vibratory excitation. These small-amplitude vibrations can be used to measure linear shear modulus in a pre-stressed tissue.

Data are then acquired with an MRI system while the dual-frequency vibratory stimulus is being applied to the subject, as indicated at step 204. The data can be acquired using any suitable MRE data acquisition scheme, in which the frequency of the motion-encoding gradients used in the data acquisition is matched with the frequency of the second, higher-frequency vibratory excitation.

The dual-frequency approach allows for measuring the linear shear properties (e.g., displacement, strain, and modulus) at different pre-deformations in vivo. Investigating the evolution of linear shear properties as a function of different states of pre-deformation can recover the shear nonlinearity of biological tissues and then facilitate tissue characterization and clinical diagnosis in diseases. Because of the first vibratory excitation, the data acquired in step 204 will indicate various different states of pre-deformation.

Images are then reconstructed from the acquired data, as indicated at step 206. Reconstruction of the images may be performed as described in U.S. Pat. No. 5,592,085, and in U.S. Pat. No. 5,825,186, both of which are incorporated herein by reference in their entirety. Because the data were acquired in step 204 while a dual-frequency vibratory stimulus was applied to the subject, images are reconstructed for each of the plurality of different pre-deformation states indicated by the dual-frequency vibratory stimulus.

Mechanical properties of the tissue under examination are then computed for each pre-deformation state based at least in part on the reconstructed images, as indicated at step 208. The mechanical properties can then be analyzed as a function of different pre-deformation states to recover nonlinear mechanical properties of the tissue under examination, as indicated at step 210.

In one non-limiting example application, haptic inflammation or portal hypertension can alter the initial preload state of the liver (e.g., via stress history from increased interstitial fluid pressure or portal pressure). Dual-frequency liver MRE-derived parameters are strongly dependent on both the initial state of stress and applied dynamic deformation/stress of selected meaningful equilibrium state. Changes in liver stiffness (i.e., 3rd and 4th-order constants of nonlinearity) can differentiate what level of deformation/stress the perturbations are applied, and are applicable only to that pathophysiologic state. Stress is related to the safety, growth, and change in the organ. Either over-stress or under-stress of a tissue may cause resorption, and change in stress level causes structural remodeling of an organ (e.g., venous congestion leads to development of hepatic fibrosis). A study of the relationship between different levels of scales would provide a deeper understanding of physiology and mechanics and the function of an organ, which can be achieved by implementing the methods described in the present disclosure.

Several challenges exist for the measurement of skull displacement using MRE. As one example challenge with measuring skull displacement using MRE, there is no skull signal present in images acquired with the standard spin echo ("SE") EPI-based MRE pulse sequence. Anatomically, the skull includes an outer cortex, the medullary space, and the inner cortex. Cortical bone has an ultrashort $T_2$ and produces no discernible signal when imaged with standard echo times (e.g., about 50 ms in EPI-MRE). The signal from the medullary cavity filled with fatty marrow is suppressed because the EPI sequence typically uses fat-suppression to avoid chemical shift-based ghost artifacts along the phase encoding direction. Given that cortical bone imaging using ultrashort TE is technically challenging for MRE acquisitions because of the presence of motion encoding gradients, it is contemplated that signal from the skull can be effectively detected by measuring the fat signal from the fatty marrow contained within the medullary cavity.

To this end, the systems and methods described in the present disclosure can implement a dual-saturation imaging scheme to acquire first data with fat-suppression and to acquire second data with water-suppression. The first data and the second data can be acquired in separate scans, or can be sequentially acquired in the same scan by automatically shifting the imaging center frequency to acquire water signal data with fat-suppression and fat signal data with water-suppression. The first data are used in the conventional manner to characterize mechanically induced motion in brain tissue. The second data are used to separately estimate the skull motion. As noted, the skull is almost always represented as a signal void on the standard MRE-EPI image that uses on-resonance water excitation and fat suppression. By using a water-suppressed acquisition, the middle layer of the skull (i.e., the medullary cavity filled with fatty marrow) has adequate signal to be analyzed and used to track skull motion. Following reconstruction, these two distinct data sets can be analyzed together to reveal the interactions between the skull and brain motion.

A full skull and brain MRE data set can be generated by combining the separately, or sequentially, acquired water-dominant signals and fat-dominant signals in the complex image domain. Because there will be some water-based signal within the medullary cavity, the dominantly fat and dominantly water images can in some examples be combined by phase preserving complex multiplication rather than direct summation, in order to give a more accurate characterization of the combined signal. An example of such a phase preserving complex combination is given as, $$S = \sqrt{|S_w| \cdot S_w + |S_f| \cdot S_f} \cdot e^{i \cdot arg(|S_w| \cdot S_w + |S_f| \cdot S_f)}; \quad (2)$$

where $S_w$ and $S_f$ are the complex images reconstructed from the water-dominant data and the fat-dominant data, respectively. The motion displacements at each phase offset can then be calculated from the combined phase data from Eqn. (2), from which mechanical properties can be estimated using MRE techniques.

Displacements from regions-of-interest ("ROIs") associated with the brain and skull can be fitted to a model of rigid-body motion to obtain rigid-body translation ($T_x$, $T_y$, and $T_z$) and rotation ($\theta_x$, $\theta_y$, $\theta_z$). The rigid-body fitting origin can be defined as the center of mass of the brain for the subject. The harmonic vibrations in MRE with multiple phase offsets can result in a set of complex translational and rotational coefficients. Several quantities can be calculated from the skull and brain motion data, including the amplitude of translational and rotational motion of the skull and brain in the x-, y-, and z-directions respectively; the ratios of brain-to-skull in the amplitude of translational and rotational motion in the x-, y-, and z-directions; the 3D trajectory of translational motion of the skull and brain, as well as their spatial angle, $\alpha$; the temporal phase delay $\varphi_T$ between the skull and brain translational motion, which can be calculated as the weighted average over the x-, y-, and z-translational phase delays weighted by the amplitude of each translational component; and the temporal phase delay, $\varphi_R$, between the skull and brain rotational motion calculated the same as the weighted average over the x-, y-, and z-rotational phase delays.

Based on these techniques, the full head motion can be estimated and the skull and brain displacement can be measured on a voxel basis, which can be used to assess how the skull-brain interface attenuates and delays motion transmission into the brain, which can in turn provide insights into the skull-brain coupling mechanisms.

Another challenge with measuring skull displacement with MRE is that during a brain MRE acquisition, the mechanical driver is in direct contact with the head, and the rigid skull experiences displacements that are considerably larger than the shear motion of brain tissue. As the motion encoding threshold of the MRE pulse sequence is set according to the expected lower shear motion of brain tissue to provide sufficient sensitivity, the motion-induced phase of the skull signal resulting from larger rigid-body displacement typically exhibits substantial wrapping in both space and time (i.e., between MRE phase offsets). A wide range of phase unwrapping algorithms have been investigated to unwrap either individual MRE wave images or the entire phase image series simultaneously. Classical unwrapping algorithms typically work well in the spatial domain, but unwrapping in time is quite challenging because of the very sparse sampling (e.g., 4-8 points per period) in MRE, especially with heavily wrapped phase across different time points.

To this end, the systems and methods described in the present disclosure also provide a dual-sensitivity motion encoding scheme for generating wrap-free phase-based estimates of skull motion simultaneously with brain motion characterization. The dual-sensitivity motion encoding scheme simultaneously acquires phase images using both low-motion encoding and high-motion encoding during a single MRE exam. The low-sensitivity phase image is both temporally and spatially wrap-free and therefore can be used to guide unwrapping of the high-sensitivity phase image to estimate the full skull and brain motion.

As noted above, in a standard MRE acquisition the motion is encoded into the MRI phase signal by motion encoding gradients. Typically, two sets of motion encoding gradients with the same amplitude, but opposite polarity, are used to acquire positive and negative phase images. Phase difference images are then calculated to remove any unwanted background phase and double the motion signal-to-noise ratio, which could lead to significant temporal and spatial phase wrapping.

Figure 4:
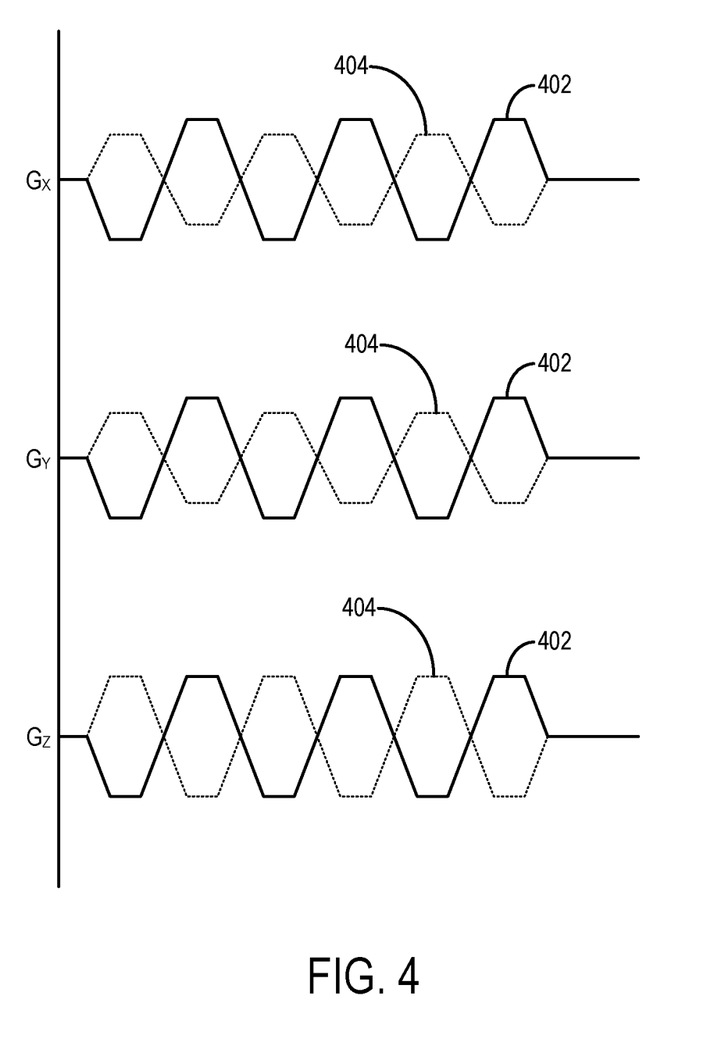
FIG. 4 is an example of a dual-sensitivity motion encoding scheme.

A separate MRE scan can be performed using a motion encoding gradient with low amplitude to achieve wrap-free phase that can be used to check the phase unwrapping; however, this would double the scan time. In some embodiments of the methods described in the present disclosure, a dual-sensitivity motion encoding scheme can be used to simultaneously acquire both low-motion encoding and high-motion encoding images. An example of a dual-sensitivity motion encoding scheme is shown in FIG. 4. In this motion encoding scheme, the amplitudes of the positive motion encoding gradients 402 and negative motion encoding gradients 404 are slightly different. In the example shown in FIG. 4, the amplitude of negative motion encoding gradients 404 is smaller than that of the positive motion encoding gradients 402; however, the reverse setup can also be used with similar effect.

In some implementations, flow compensation gradients can be added before the motion encoding gradients along one or more gradient axes. For instance, a flow compensation gradient can be applied on the $G_z$ axis prior to the negative motion encoding gradient, but not the positive motion encoding gradient, applied along that same gradient axis.

Using a dual-sensitivity motion encoding scheme, high-sensitivity phase images, $\Phi$, can be generated in a standard manner by subtraction of the signals from the positive and negative motion encoding gradients, whereas the low-sensitivity phase data, $\varphi$, which will typically not exhibit any phase wrap (both spatially and temporally), is calculated by adding these signals from the positive and negative motion encoding gradients. With this approach, both low and high motion encoding sensitivity data can be acquired simultaneously during a single exam. Because the ratio of the two sensitivities is known, the low-sensitivity data, $\varphi$, can be used to estimate and guide the unwrapping of the high-sensitivity data, $\Phi$. The phase estimation can be performed, for instance, on the first temporal harmonic of the phase offsets and then projected to each phase offset for unwrapping.

In detail, in a steady-state MRE experiment with monodirectional encoding, the relation between the first harmonic component of the displacement, d, and the first harmonic of the time-domain phase signal, $\theta_\pm$, can be described as, $$\theta_\pm = M_\pm d; \qquad (3)$$

where M is a 3×3 encoding matrix, and ± denotes the polarity of the motion encoding gradients. The quantities in bold represent the complex first harmonic.

Taking all imaging gradients into account, the effective positive and negative encoding matrices can be written as, $$M_+ = \begin{bmatrix} M+m_x & m_y & m_z \\ m_x & M+m_y & m_z \\ m_x & m_z & M+m_z \end{bmatrix}; \qquad (4)$$

$$M_- = \begin{bmatrix} -k_1 M+m_x & m_y & m_z \\ m_x & -k_2 M+m_y & m_z \\ m_x & m_z & -k_3 M+m_z \end{bmatrix}; \qquad (5)$$

where M is the motion sensitivity of the motion encoding gradients; $m_x$, $m_y$, and $m_z$ are the motion sensitivities of the x-imaging, y-imaging, and z-imaging gradients, respectively; and $k_1$, $k_2$, and $k_3 \in (0,1]$ are the scale factors of the negative motion encoding gradients relative to the positive motion encoding gradients. It will be appreciated that when the amplitudes of the positive motion encoding gradients are scaled differently from the negative motion encoding gradients that the scale factors will be present instead in the positive encoding matrix.

The high-sensitivity harmonic, $\Phi$, which will typically exhibit significant phase wrapping, can be calculated by subtraction of the signal from the positive and negative motion encoding gradients (i.e., the positive and negative phase data), $$\Phi = (\theta_+ - \theta_-) = (M_+ - M_-)d. \qquad (6)$$

It is noted that $(M_+ - M_-)$ is a diagonal matrix where $m_x$, $m_y$, and $m_z$ cancel out.

The low sensitivity harmonic, $\varphi$, which will typically not exhibit any spatial or temporal phase wrapping, can be calculated by adding the harmonic signals as, $$\varphi = (\theta_+ + \theta_-) = (M_+ + M_-)d. \qquad (7)$$

Although the unwanted background phase may not be completely removed after phase summation, it is constant over time so it can be filtered out by taking the first temporal harmonic of the wrap-free low-sensitivity data.

As will be described below, the positive and negative phase data acquired using this dual-sensitivity motion encoding scheme can be used to compute high-sensitivity and low-sensitivity harmonics, which can be used in turn to generate phase unwrapped images.

Figure 5:
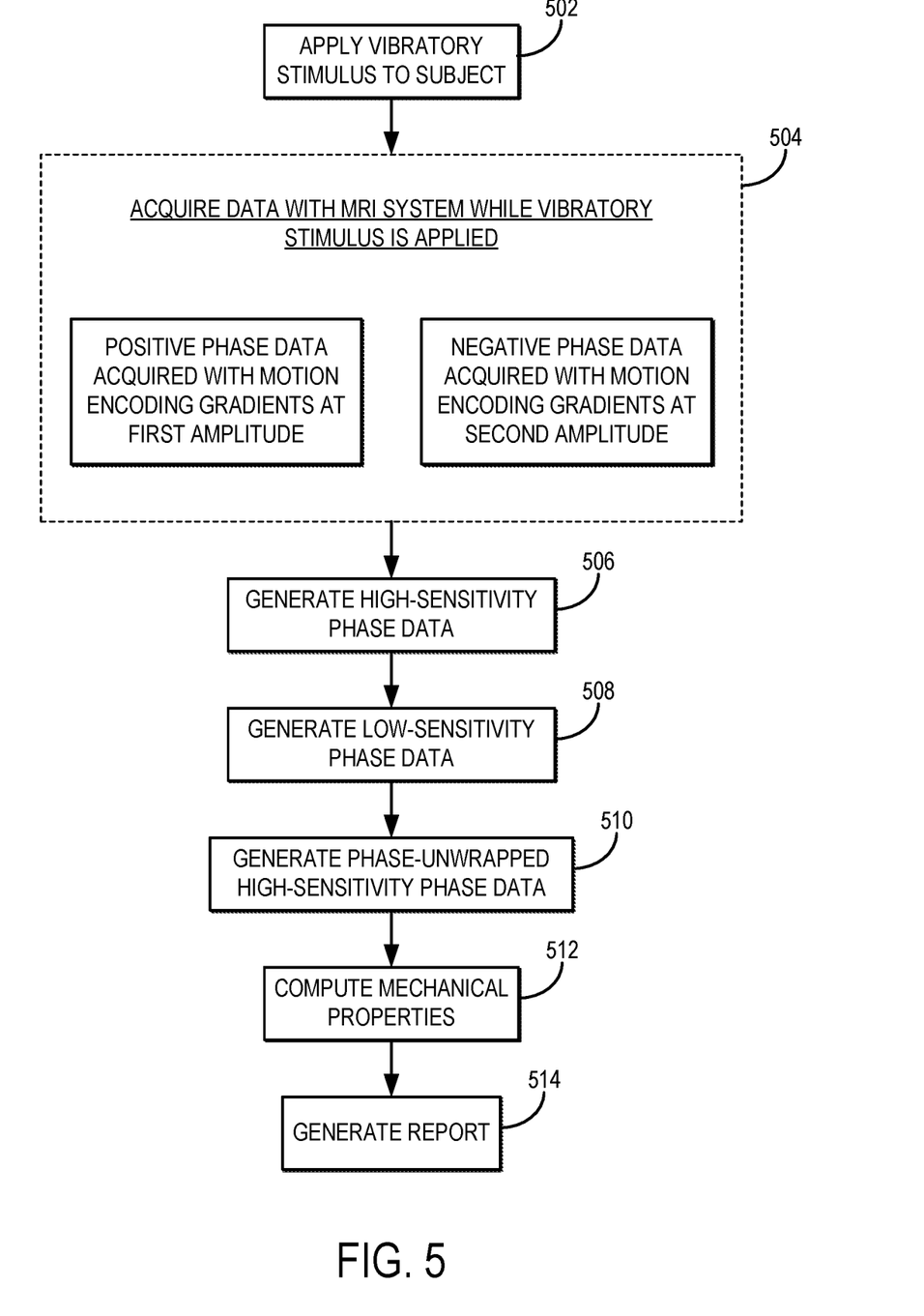
FIG. 5 is flowchart setting forth the steps of an example method for implementing MRE using a dual-sensitivity motion encoding scheme.

Referring now to FIG. 5, a flowchart is illustrated as setting forth the steps of an example method for implementing MRE using a dual-sensitivity motion encoding scheme. The method includes applying a vibratory stimulus to the subject (e.g., the subject's head), as indicated at step 502. As described above, the vibratory stimulus can be provided by an MRE driver. In some embodiments, the MRE driver may include an MRE driver system that is coupled to the subject's head and used to impart vibration energy to the subject's skull and brain, which in turn introduces relative shear motions (e.g., in the range of microns) between the brain and the skull.

Data are then acquired from the subject with an MRI system while the vibratory stimulus is applied, as indicated at step 504. In general, the data are acquired using a pulse sequence that includes a dual-sensitivity motion encoding scheme, which as described above includes applying opposite polarity motion encoding gradients with different amplitudes rather than the same amplitude. The acquired data can therefore include first data acquired with positive polarity motion encoding gradients and second data acquired with negative polarity motion encoding gradients. The first and second data can be acquired in separate scans, or can be sequentially acquired in a single scan. As in conventional motion encoding schemes, the motion encoding gradients are synchronized with the applied vibratory stimulus such that the shear motions caused by the vibratory stimulus are encoded into the acquired magnetic resonance signals.

As noted, the acquired data include positive phase data and negative phase data. Positive phase data are acquired using an acquisition in which the polarity of the motion encoding gradients is selected to be in-phase with the imparted motion and using a first amplitude for the motion encoding gradients. Similarly, negative phase data are acquired are acquired using an acquisition in which the polarity of the motion encoding gradients is inverted, such that the motion encoding gradients are out-of-phase with the imparted motion, and in which a second amplitude is used for the motion encoding gradients. As described above, the first amplitude and the second amplitude are generally different; however, in instances where motion encoding gradients are simultaneously applied along different gradient axes, the amplitudes may only be different along some and not all of the gradient axes, such as in the example shown in FIG. 4. The amplitude may vary for each motion encoding direction, or only some of the motion encoding directions (e.g., $G_X$ and $G_Y$ as shown in FIG. 4).

High-sensitivity phase data, $\Phi$, are generated by computing a difference between the positive phase data and the negative phase data, as indicated at step 506, and described above. Low-sensitivity data, φ, are also generated by computing a sum of the positive phase data and the negative phase data, as indicated at step 508, and described above. Because Φ and φ both linearly encode the harmonic motion, d, phase synthesized from the low-sensitivity signal, φ, which, by carefully selecting k, will be essentially wrap-free, can be used to guide unwrapping of the phase synthesized from the high-sensitivity signal, Φ.

The high-sensitivity phase data are then phase unwrapped using the low-sensitivity phase data, as indicated at step 510. First, an estimate of the high-sensitivity harmonic signal, $\hat{\Phi}_{syn}$, is calculated as, $$\hat{\Phi}_{syn} = T\varphi; \quad (8)$$

where T is a 3×3 estimation matrix defined by, $$T = (M_+ - M_-)(M_+ + M_-)^{-1}. \quad (9)$$

In the example of the encoding scheme shown in FIG. 4, $m_x$ and $m_y$ are negligible. But, when flow-compensation gradients are implemented in the z-axis, these gradients will encode some amount of motion into the low-sensitivity encoded phase, $\varphi_x$ and $\varphi_y$, resulting in large estimation errors if not corrected for. To address this problem, the amplitude of the motion encoding gradient in the z-direction is set to be equal in the positive and negative encoding steps (i.e., $k_3=1$), as shown in FIG. 4, but the z-axis flow compensation gradients are used to provide the low-motion-sensitivity. In this way, the harmonic $\varphi_x$ and $\varphi_y$ can then be corrected by subtracting out $\varphi_z$. With negligible motion encoding from other imaging gradients except for the flow compensation gradients in the z-direction, and with $k_1=k_2=k$, the estimation matrix, T, can be presented as, $$T = \begin{bmatrix} \frac{1+k}{1-k} & 0 & -\frac{1+k}{1-k} \\ 0 & \frac{1+k}{1-k} & -\frac{1+k}{1-k} \\ 0 & 0 & \frac{M}{m_z} \end{bmatrix}. \quad (10)$$

Of note, because the flow compensation gradient and motion encoding gradients have different temporal phase shifts relative to the vibratory motion, $m_z$ is also a complex number, and its angle represents its relative phase delay to the motion encoding gradients.

From Eqns. (8) and (10), the estimate of the high-sensitivity harmonic from the low-sensitivity harmonic φ can then be written as, $$\hat{\Phi}_{syn,x} = \frac{1+k}{1-k}(\varphi_x - \varphi_z) \quad (11)$$

$$\hat{\Phi}_{syn,y} = \frac{1+k}{1-k}(\varphi_y - \varphi_z)$$

$$\hat{\Phi}_{syn,x} = \frac{M}{m_z}\varphi_z;$$

The harmonics can then be projected back to the time domain, and the phase maps at each phase offset computed as, $$\hat{\Phi}_{syn,x,y,z}(t) = \text{Re}\left\{\hat{\Phi}_{syn,x,y,z} \cdot e^{\frac{i2\pi t}{T}}\right\}; \quad (12)$$

where T is the period of the vibratory stimulus.

Finally, the high-sensitivity phase data, Φ, at each phase offset can be unwrapped as, $$\Phi_{uw}(t) = \Phi(t) + \text{Round}\left\{\frac{(\hat{\Phi}_{syn}(t) - \Phi(t))}{2\pi}\right\} \cdot 2\pi; \quad (13)$$

where Round {•} represents a rounding function, which may be a nearest integer function.

Mechanical properties can then be estimated from the phase unwrapped, high-sensitivity phase data, as indicated at step 512 using conventional MRE techniques. For instance, wave images can be reconstructed and an inversion algorithm can be applied to the wave images to estimate mechanical properties, such as shear stiffness. For instance, mechanical properties of the tissue under examination can be computed in accordance with traditional MRE techniques, such as those described in U.S. Pat. No. 5,592,085, and in U.S. Pat. No. 5,825,186, both of which are incorporated herein by reference in their entirety. When images are acquired according to SII techniques, mechanical properties such as octahedral shear strain can be computed.

The computed mechanical properties can then be analyzed to measure or otherwise assess a tissue state in the subject, such as trabecular reserve, and a report indicating the assessment or measurement of this tissue state can be generated, as indicated at step 514. As an example, the mechanical properties can be compared to stored values associated with different states of trabecular reserve or other tissue states. For instance, in general, the loss of trabecular reserve will change the relative displacements between the brain and skull, and these changes can be assessed by comparing the measured mechanical properties to stored values associated with known levels of trabecular reserve.

In some instances, the mechanical properties can be compared with values previously computed for the same subject, in which case changes in the subject's own mechanical properties would indicate loss of trabecular reserve.

In some other instances, the report may include generating and displaying mechanical property maps, which depict the spatial distribution of a particular mechanical property in the subject, as measured using the MRE techniques described above.

By using the dual-sensitivity motion encoded schemes described above, and the associated guided phase unwrapping procedure, wrap-free estimates of both skull and brain phase signals can be generated, even when only as few as four MRE phase offsets were acquired: a scenario where conventional phase unwrapping algorithms often fail.

Figure 6:
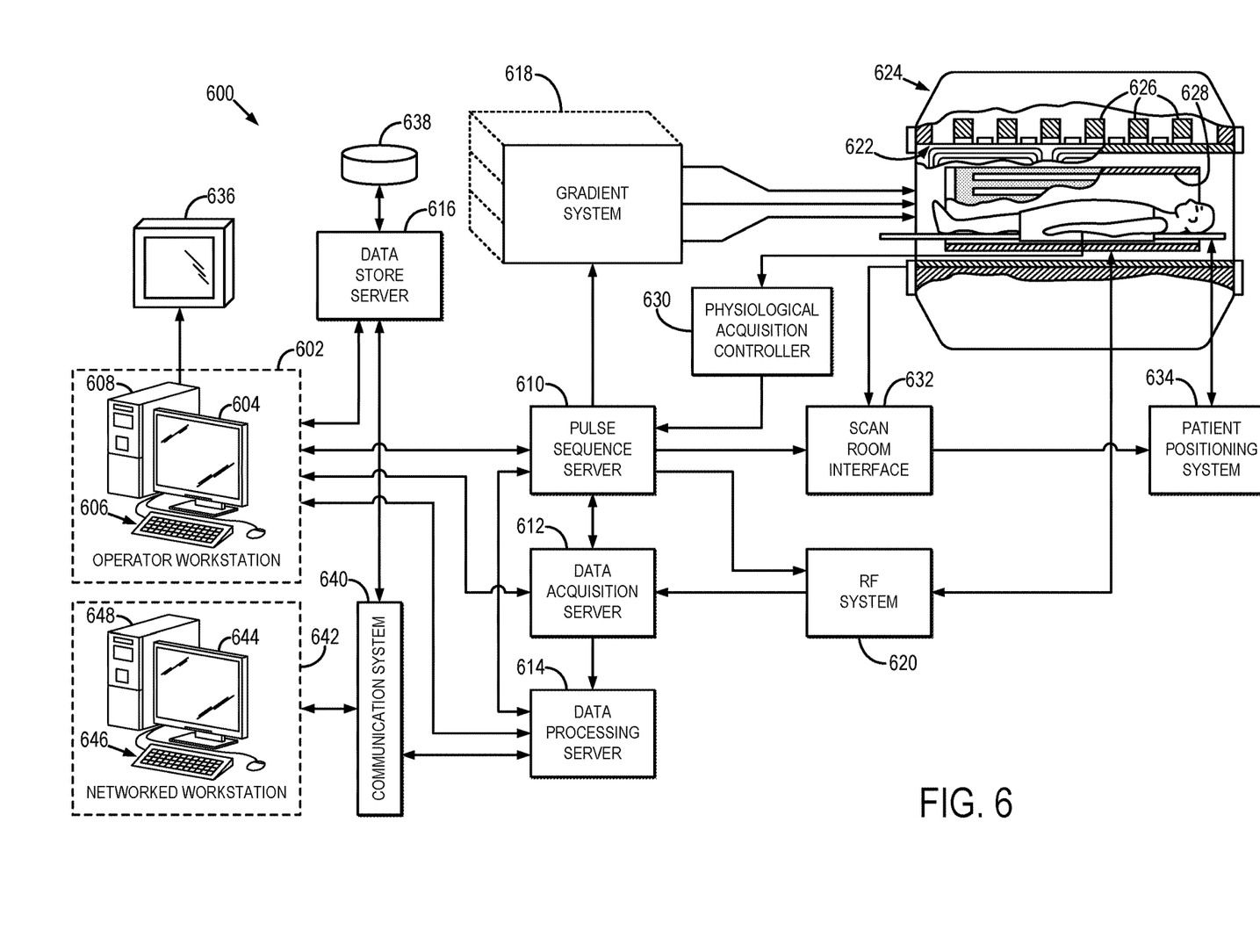
FIG. 6 is a block diagram of an example magnetic resonance imaging ("MRI") system that can implement the methods described in the present disclosure.

Referring particularly now to FIG. 6, an example of an MRI system 600 that can implement the methods described here is illustrated. The MRI system 600 includes an operator workstation 602 that may include a display 604, one or more input devices 606 (e.g., a keyboard, a mouse), and a processor 608. The processor 608 may include a commercially available programmable machine running a commercially available operating system. The operator workstation 602 provides an operator interface that facilitates entering scan parameters into the MRI system 600. The operator workstation 602 may be coupled to different servers, including, for example, a pulse sequence server 610, a data acquisition server 612, a data processing server 614, and a data store server 616. The operator workstation 602 and the servers 610, 612, 614, and 616 may be connected via a communication system 640, which may include wired or wireless network connections.

The pulse sequence server 610 functions in response to instructions provided by the operator workstation 602 to operate a gradient system 618 and a radiofrequency ("RF") system 620. Gradient waveforms for performing a prescribed scan are produced and applied to the gradient system 618, which then excites gradient coils in an assembly 622 to produce the magnetic field gradients $G_x$, $G_y$, and $G_z$ that are used for spatially encoding magnetic resonance signals. The gradient coil assembly 622 forms part of a magnet assembly 624 that includes a polarizing magnet 626 and a whole-body RF coil 628.

RF waveforms are applied by the RF system 620 to the RF coil 628, or a separate local coil to perform the prescribed magnetic resonance pulse sequence. Responsive magnetic resonance signals detected by the RF coil 628, or a separate local coil, are received by the RF system 620. The responsive magnetic resonance signals may be amplified, demodulated, filtered, and digitized under direction of commands produced by the pulse sequence server 610. The RF system 620 includes an RF transmitter for producing a wide variety of RF pulses used in MRI pulse sequences. The RF transmitter is responsive to the prescribed scan and direction from the pulse sequence server 610 to produce RF pulses of the desired frequency, phase, and pulse amplitude waveform. The generated RF pulses may be applied to the whole-body RF coil 628 or to one or more local coils or coil arrays.

The RF system 620 also includes one or more RF receiver channels. An RF receiver channel includes an RF preamplifier that amplifies the magnetic resonance signal received by the coil 628 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} ; \quad (14)$$

and the phase of the received magnetic resonance signal may also be determined according to the following relationship:

$$\varphi = \tan^{-1}\left(\frac{Q}{I}\right). \quad (15)$$

The pulse sequence server 610 may receive patient data from a physiological acquisition controller 630. By way of example, the physiological acquisition controller 630 may receive signals from a number of different sensors connected to the patient, including electrocardiograph ("ECG") signals from electrodes, or respiratory signals from a respiratory bellows or other respiratory monitoring devices. These signals may be used by the pulse sequence server 610 to synchronize, or "gate," the performance of the scan with the subject's heart beat or respiration.

The pulse sequence server 610 may also connect to a scan room interface circuit 632 that receives signals from various sensors associated with the condition of the patient and the magnet system. Through the scan room interface circuit 632, a patient positioning system 634 can receive commands to move the patient to desired positions during the scan.

The digitized magnetic resonance signal samples produced by the RF system 620 are received by the data acquisition server 612. The data acquisition server 612 operates in response to instructions downloaded from the operator workstation 602 to receive the real-time magnetic resonance data and provide buffer storage, so that data is not lost by data overrun. In some scans, the data acquisition server 612 passes the acquired magnetic resonance data to the data processor server 614. In scans that require information derived from acquired magnetic resonance data to control the further performance of the scan, the data acquisition server 612 may be programmed to produce such information and convey it to the pulse sequence server 610. For example, during pre-scans, magnetic resonance data may be acquired and used to calibrate the pulse sequence performed by the pulse sequence server 610. As another example, navigator signals may be acquired and used to adjust the operating parameters of the RF system 620 or the gradient system 618, or to control the view order in which k-space is sampled. In still another example, the data acquisition server 612 may also process magnetic resonance signals used to detect the arrival of a contrast agent in a magnetic resonance angiography ("MRA") scan. For example, the data acquisition server 612 may acquire magnetic resonance data and processes it in real-time to produce information that is used to control the scan.

The data processing server 614 receives magnetic resonance data from the data acquisition server 612 and processes the magnetic resonance data in accordance with instructions provided by the operator workstation 602. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 614 are conveyed back to the operator workstation 602 for storage. Real-time images may be stored in a data base memory cache, from which they may be output to operator display 602 or a display 636. Batch mode images or selected real time images may be stored in a host database on disc storage 638. When such images have been reconstructed and transferred to storage, the data processing server 614 may notify the data store server 616 on the operator workstation 602. The operator workstation 602 may be used by an operator to archive the images, produce films, or send the images via a network to other facilities.

The MRI system 600 may also include one or more networked workstations 642. For example, a networked workstation 642 may include a display 644, one or more input devices 646 (e.g., a keyboard, a mouse), and a processor 648. The networked workstation 642 may be located within the same facility as the operator workstation 602, or in a different facility, such as a different healthcare institution or clinic.

The networked workstation 642 may gain remote access to the data processing server 614 or data store server 616 via the communication system 640. Accordingly, multiple networked workstations 642 may have access to the data processing server 614 and the data store server 616. In this manner, magnetic resonance data, reconstructed images, or other data may be exchanged between the data processing server 614 or the data store server 616 and the networked workstations 642, such that the data or images may be remotely processed by a networked workstation 642.

The present disclosure has described one or more preferred embodiments, and it should be appreciated that many equivalents, alternatives, variations, and modifications, aside from those expressly stated, are possible and within the scope of the invention.

The invention claimed is:

1. A method for quantifying trabecular reserve with magnetic resonance imaging (MRI), the steps of the method comprising:
    (a) applying a vibratory motion to a subject's head to impart shear motions between a skull and a brain of the subject;
    (b) acquiring data with an MRI system using a pulse sequence that includes motion encoding gradients having a frequency synchronized with a frequency of the applied vibratory motion;
    (c) reconstructing images from the acquired data;
    (d) computing mechanical properties of a sub-arachnoid space from the reconstructed images; and
    (e) generating a report that indicates trabecular reserve in the subject based on the mechanical properties of the sub-arachnoid space.

2. The method as recited in claim 1, wherein step (e) comprises comparing the mechanical properties of the sub-arachnoid space computed in step (d) with stored mechanical property values that are stored in a data storage.

3. The method as recited in claim 2, wherein the stored mechanical property values indicate a particular tissue state.

4. The method as recited in claim 3, wherein the particular tissue state is a particular level of trabecular reserve.

5. The method as recited in claim 2, wherein the stored mechanical property values are mechanical property values that were previously computed for the subject.

6. The method as recited in claim 1, wherein the images reconstructed in step (c) indicate intravoxel phase dispersion associated with a tissue interface between the subject's brain and the subject's skull.

7. The method as recited in claim 6, wherein the mechanical properties computed in step (d) include octahedral shear strain values.

8. The method as recited in claim 1, wherein the vibratory motion applied to the subject's head comprises a first vibratory motion oscillating at a first frequency and a second vibratory motion oscillating at a second frequency that is greater than the first frequency.

9. The method as recited in claim 8, wherein the first frequency is less than 5 Hz.

10. The method as recited in claim 9, wherein the second frequency is 60 Hz.

11. The method as recited in claim 8, wherein the frequency of the motion encoding gradients is synchronized with the second frequency of the vibratory motion.

12. The method as recited in claim 8, wherein the first vibratory motion indicates a plurality of different pre-deformation states, step (c) includes reconstructing images for each of the plurality of different pre-deformation states.

13. The method as recited in claim 12, wherein step (d) includes computing nonlinear mechanical properties based on the images reconstructed for each of the plurality of different pre-deformation states.

14. The method as recited in claim 1, wherein the data acquired in step (b) comprise first motion encoded data in which fat signals are suppressed and second motion encoded data in which water signals are suppressed.

15. The method as recited in claim 14, wherein the first motion encoded data are acquired following a water-selective spatial-spectral excitation and the second motion encoded data are acquired following a fat-selective spatial-spectral excitation.

16. The method as recited in claim 14, wherein step (c) includes reconstructing the images by reconstructing first images from the first motion encoded data, reconstructing second images from the second motion encoded data, and combining the first images and the second images.

17. The method as recited in claim 16, wherein combining the first images and the second images includes combining the first images and the second images using a phase preserving complex combination.

18. The method as recited in claim 1, wherein step (b) includes acquiring first motion encoding data using motion encoding gradients with a first amplitude and a first polarity and second motion encoding data using motion encoding gradients with a second amplitude that is different from the first amplitude and a second polarity that is opposite the first polarity.

19. The method as recited in claim 18, wherein step (c) includes reconstructing phase unwrapped images from the acquired data by:
    reconstructing first images from the first motion encoding data;
    reconstructing second images from the second motion encoding data;
    generating high-sensitivity phase data by computing a difference between the first images and the second images;
    generating low-sensitivity phase data by computing a summation between the first images and the second images; and
    phase unwrapping the high-sensitivity phase data using the low-sensitivity phase data.

20. The method as recited in claim 19, wherein phase unwrapping the high-sensitivity data comprises estimating a high-sensitivity harmonic from the low-sensitivity data and using the high-sensitivity harmonic to phase unwrap the high-sensitivity phase data.

21. A method for quantifying nonlinear mechanical properties of a tissue using magnetic resonance imaging (MRI), the steps of the method comprising:
    (a) applying a dual-frequency vibratory motion to a subject to impart shear motions in a tissue of interest in the subject, wherein the dual-frequency vibratory motion comprises a first vibratory motion oscillating at a first frequency and a second vibratory motion oscillating at a second frequency that is greater than the first frequency;
    (b) acquiring data with an MRI system using a pulse sequence that includes motion encoding gradients having a frequency synchronized with the second frequency of the applied vibratory motion;

(c) reconstructing images from the acquired data;

(d) computing mechanical properties of the tissue of interest from the reconstructed images; and (e) generating a report that indicates the computed mechanical properties of the tissue of interest.

22. The method as recited in claim 21, wherein the first vibratory motion indicates a plurality of different pre-deformation states, step (c) includes reconstructing images for each of the plurality of different pre-deformation states.

23. The method as recited in claim 22, wherein step (d) includes computing nonlinear mechanical properties based on the images reconstructed for each of the plurality of different pre-deformation states.

24. The method as recited in claim 21, wherein the first frequency is less than 5 Hz.

25. The method as recited in claim 24, wherein the second frequency is greater than 60 Hz.

26. The method as recited in claim 24, wherein the second frequency is 60 Hz.

27. The method as recited in claim 21, wherein the tissue of interest is the subject's liver.

28. The method as recited in claim 21, wherein the tissue of interest corresponds to a sub-arachnoid space between the subject's brain and the subject's skull.

29. A method for dual-saturation magnetic resonance elastography (MRE) using a magnetic resonance imaging (MRI) system, the steps of the method comprising:

(a) applying a vibratory motion to a subject to impart vibratory motion in a region-of-interest in the subject;

(b) acquiring first data with an MRI system using a first pulse sequence that includes a first motion encoding gradients whose frequency is synchronized with a frequency of the applied vibratory motion, wherein fat signals are suppressed in the first data;

(c) acquiring second data with the MRI system using a second pulse sequence that includes second motion encoding gradients whose frequency is synchronized with the frequency of the applied vibratory motion, wherein water signals are suppressed in the second data;

(d) reconstructing first images from the first data, wherein the first images depict a water-dominant signal;

(e) reconstructing second images from the second data, wherein the second images depict a fat-dominant signal; and (f) generating combined images by combining the first images and the second images.

30. The method as recited in claim 29, wherein the first images and the second images are combined in step (f) using a phase preserving complex combination.

31. The method as recited in claim 29, further comprising computing mechanical properties in the region-of-interest from the combined images.

32. The method as recited in claim 31, further comprising generating a mechanical property map from the computed mechanical properties, wherein the mechanical property map depicts a spatial distribution of the computed mechanical properties in the region-of-interest in the subject.

33. A method for generating phase unwrapped images from data acquired during a magnetic resonance elastography (MRE) acquisition using a magnetic resonance imaging (MRI) system, the steps of the method comprising:

(a) applying a vibratory motion to a subject to impart vibratory motion in a region-of-interest in the subject;

(b) acquiring first data with an MRI system using a first pulse sequence that includes first motion encoding gradients having a first amplitude, a positive polarity, and whose frequency is synchronized with a frequency of the applied vibratory motion;

(c) acquiring second data with the MRI system using a second pulse sequence that includes second motion encoding gradients having a second amplitude, a negative polarity, and whose frequency is synchronized with the frequency of the applied vibratory motion;

(d) reconstructing first images from the first data and second images from the second data, wherein the first images and the second images are complex images having magnitude data and phase data;

(e) generating high-sensitivity phase data by computing a difference of the phase data in the first images and the second images;

(f) generating low-sensitivity phase data by computing a summation of the phase data in the first images and the second images; and (g) generating phase unwrapped data using the low-sensitivity phase data to guide phase unwrapping of the high-sensitivity data.

34. The method as recited in claim 33, further comprising computing mechanical properties in the region-of-interest from the phase unwrapped data.

35. The method as recited in claim 34, further comprising generating a mechanical property map from the computed mechanical properties, wherein the mechanical property map depicts a spatial distribution of the computed mechanical properties in the region-of-interest in the subject.

\* \* \* \* \*